(12) United States Patent
Garcia et al.

(10) Patent No.: US 10,330,754 B2
(45) Date of Patent: Jun. 25, 2019

(54) STATOR-LESS ELECTRIC MOTOR FOR A MAGNETIC RESONANCE IMAGING SYSTEM AND METHODS THEREOF

(71) Applicant: General Electric Company, Schenectady, NY (US)

(72) Inventors: Daniel Garcia, Pewaukee, WI (US); Tamer Fahed Khalaf, Waukesha, WI (US); Jason Monclair Pittman, Waukesha, WI (US); Anton Linz, Waukesha, WI (US); William John Bonneau, Waukesha, WI (US); Chinmoy Goswami, Waukesha, WI (US); Vandana Rallabandi, Lexington, KY (US); Rahul Radhakrishna Pillai, Bangalore (IN); Srinivas Satya Sai Mallampalli, Bangalore (IN); Suma Memana Narayana Bhat, Bangalore (IN); Viswanathan Kanakasabai, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 147 days.

(21) Appl. No.: 15/396,968

(22) Filed: Jan. 3, 2017

(65) Prior Publication Data

US 2018/0188340 A1    Jul. 5, 2018

(51) Int. Cl.
| | | |
|---|---|---|
| *G01V 3/00* | (2006.01) | |
| *G01R 33/38* | (2006.01) | |
| *H02K 7/14* | (2006.01) | |
| *H02K 11/04* | (2016.01) | |
| *H02K 13/00* | (2006.01) | |
| *A61B 5/055* | (2006.01) | |
| *H02K 1/24* | (2006.01) | |

(Continued)

(52) U.S. Cl.
CPC .......... *G01R 33/3804* (2013.01); *A61B 5/055* (2013.01); *G01R 33/28* (2013.01); *H02K 1/24* (2013.01); *H02K 7/14* (2013.01); *H02K 11/044* (2013.01); *H02K 11/215* (2016.01); *H02K 13/006* (2013.01); *G01R 33/3815* (2013.01); *H02P 25/02* (2013.01)

(58) Field of Classification Search
USPC ...................................................... 324/307
See application file for complete search history.

(56) References Cited

U.S. PATENT DOCUMENTS 3,390,290 A    6/1968    Kaplan
3,925,696 A   12/1975    Popov et al.
(Continued)

FOREIGN PATENT DOCUMENTS

CN    101783557 B    3/2012
CN    202586693 U    12/2012
(Continued)

*Primary Examiner* — Rodney E Fuller
(74) *Attorney, Agent, or Firm* — Grogan, Tuccillo & Vanderleeden, LLP

(57) ABSTRACT

A stator-less electric motor for an MRI system is provided. The stator-less electric motor includes a body, a rotor rotatable connected to the body, and at least one coil winding disposed on the rotor. The at least one coil winding is arranged so as to rotate the rotor when energized via an electrical current in the presence of a magnetic field generated by a magnet assembly of the MRI system.

22 Claims, 8 Drawing Sheets

(51) Int. Cl.
  *H02K 11/215* (2016.01)
  *G01R 33/28* (2006.01)
  *G01R 33/3815* (2006.01)
  *H02P 25/02* (2016.01)

(56) References Cited

U.S. PATENT DOCUMENTS

| | | | |
|---|---|---|---|
| 5,313,131 A | 5/1994 | Hibino et al. | |
| 5,841,278 A * | 11/1998 | Green | G01R 33/3657 |
| | | | 324/318 |
| 6,914,362 B2 | 7/2005 | Lungu | |
| 7,466,053 B1 * | 12/2008 | Radev | H02K 1/32 |
| | | | 310/114 |
| 8,169,109 B2 | 5/2012 | Sykes et al. | |
| 2014/0070651 A1 | 3/2014 | Gerfast | |
| 2015/0301134 A1 * | 10/2015 | Hoshino | G01R 33/31 |
| | | | 324/307 |

FOREIGN PATENT DOCUMENTS

| | | |
|---|---|---|
| JP | H0219123 Y2 | 5/1990 |
| KR | 10-2010-0028250 A | 3/2010 |

\* cited by examiner

STATOR-LESS ELECTRIC MOTOR FOR A MAGNETIC RESONANCE IMAGING SYSTEM AND METHODS THEREOF

BACKGROUND

Technical Field

Embodiments of the invention relate generally to magnetic resonance imaging ("MRI") systems, and more specifically, to a stator-less electric motor for an MRI system and methods thereof.

Discussion of Art

MRI is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclei in the subject to be imaged. The nuclei are excited by a radio frequency ("RF") signal/pulse transmitted by a RF coil at characteristics NMR (Larmor) frequencies. By spatially disturbing localized magnetic fields surrounding the subject and analyzing the resulting RF responses from the nuclei as the excited protons relax back to their lower energy normal state, a map or image of these nuclei responses as a function of their spatial location is generated and displayed. An image of the nuclei responses provides a non-invasive view of a subject's internal structure.

Many MRI systems utilize blowers powered by electric motors to cool electronics within the same general area as the superconductive magnets. Many such electric motors, however, include ferrous components, e.g., stators, in which the strong magnetic field imposed by the superconductive magnets may induce a magnetic force without the components being energized by an electrical current. Accordingly, the ferrous components of many such electric motors are attracted towards the center of the strong magnetic field, e.g., towards the superconductive magnets, when the electric motors are not in use. Under certain circumstances, the attraction of the ferrous components within such electric motors may cause the electric motors to aggressively move towards the superconductive magnets at high speeds. Such aggressive movements of the electric motors, however, may cause severe bodily harm to individuals struck by the electric motors and/or pinned against the superconductive magnets by the electric motors.

What is needed, therefore, is a stator-less electric motor for an MRI system and methods thereof.

BRIEF DESCRIPTION

In an embodiment, a stator-less electric motor for an MRI system is provided. The stator-less electric motor includes a body, a rotor rotatable connected to the body, and at least one coil winding disposed on the rotor. The at least one coil winding is arranged so as to rotate the rotor when energized via an electrical current in the presence of a magnetic field generated by a magnet assembly of the MRI system.

In another embodiment, a method of powering a stator-less electric motor is provided. The method includes: generating a magnetic field via a magnet assembly of an MRI system; energizing at least one coil winding via an electrical current, the at least one coil winding disposed within the magnetic field on a rotor rotatable connected to a body of the stator-less electric motor; and rotating the rotor via the one or more energized coil windings in the presence of the magnetic field.

In yet another embodiment, an MRI system is provided. The MRI system includes a magnet assembly operative to generate a magnetic field, and a stator-less electric motor. The stator-less motor includes a body, a rotor ratably connected to the body, and at least one coil winding disposed on the rotor. The at least one coil winding is arranged so as to rotate the rotor when energized via an electrical current in the presence of the magnetic field.

DRAWINGS

The present invention will be better understood from reading the following description of non-limiting embodiments, with reference to the attached drawings, wherein below:

DETAILED DESCRIPTION

Figure 1:
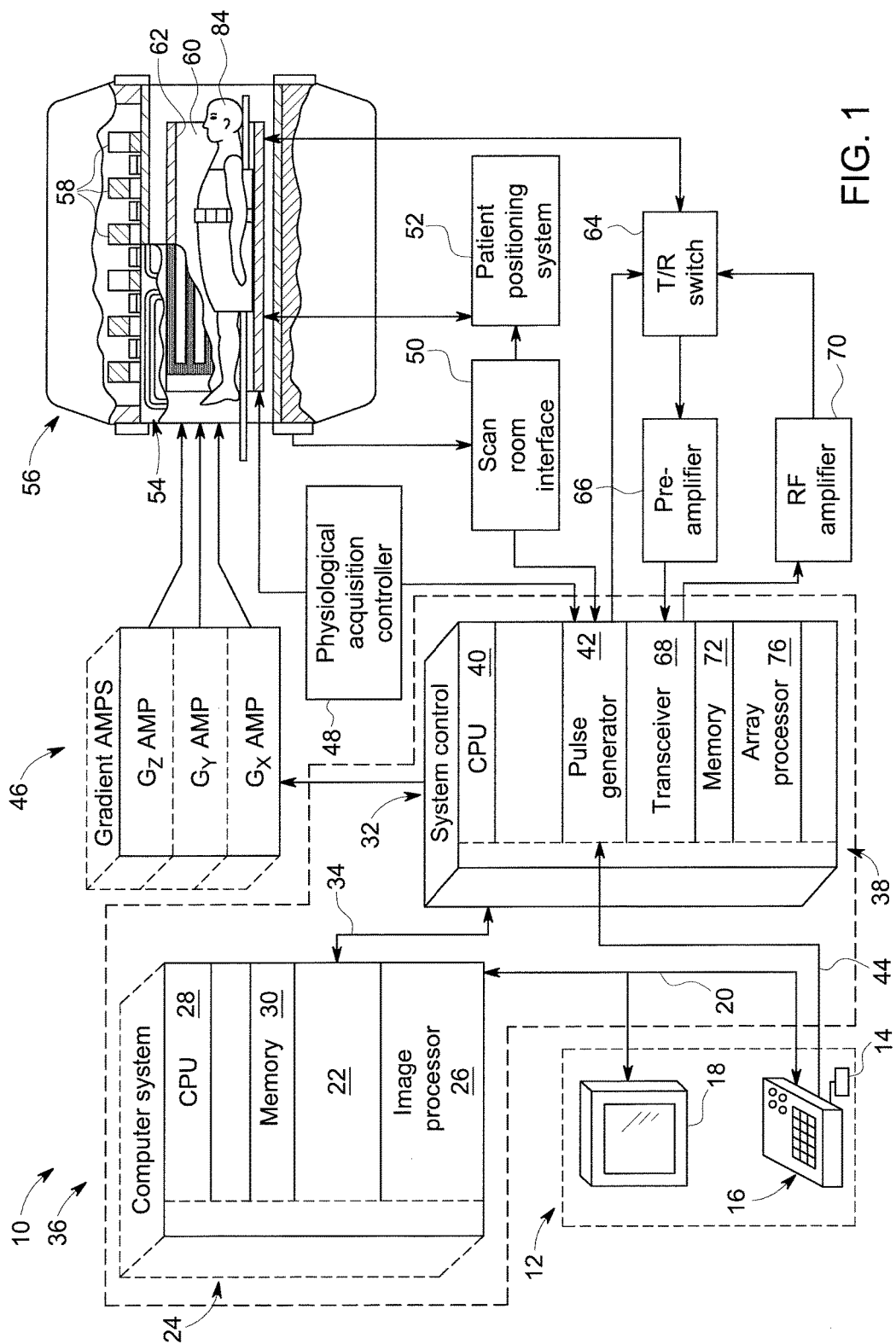
FIG. 1 is a block diagram of an exemplary MRI system in accordance with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to an MRI system, it is to be understood that embodiments of the present invention may be applicable to other systems and methods that utilize strong magnetic fields. Further still, as will be appreciated, embodiments of the present invention may be used to analyze tissue generally and are not limited to human tissue.

Referring now to FIG. 1, the major components of an MRI system 10 incorporating an embodiment of the invention are shown. Operation of the system 10 is controlled from the operator console 12, which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, which communicate with each other through a backplane 24. These include an image processor module 26, a CPU module 28 and a memory module 30, which may include a frame buffer for storing image data arrays. The computer system 22 communicates with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

The MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field $B_0$ throughout a target volume/bore 60 that is enclosed by the magnet assembly 56) and a whole-body (transmit and receive) RF coil 62 (which, in operation, provides a transverse magnetic field $B_1$ that is generally perpendicular to $B_0$ throughout the target volume 60).

The resulting signals emitted by the excited nuclei in the patient may be sensed by the same RF coil 62 and coupled through the transmit/receive switch 64 to a preamplifier 66. The amplifier Magnetic Resonance ("MR") signals are demodulated, filtered, and digitized in the receiver section of a transceiver 68. The transmit/receive switch 64 is controlled by a signal from the pulse generator module 42 to electrically connect an RF amplifier 70 to the RF coil 62 during the transmit mode and to connect the preamplifier 66 to the RF coil 62 during the receive mode. The transmit/receive switch 64 can also enable a separate RF coil (for example, a surface coil) to be used in either transmit or receive mode.

The MR signals picked up by the RF coil 62 are digitized by the transceiver module 68 and transferred to a memory module 72 in the system control 32. A scan is complete when an array of raw k-space data has been acquired in the memory module 72. This raw k-space data/datum is rearranged into separate k-space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26 and conveyed to the operator console 12 and presented on the display 18.

Figure 2:
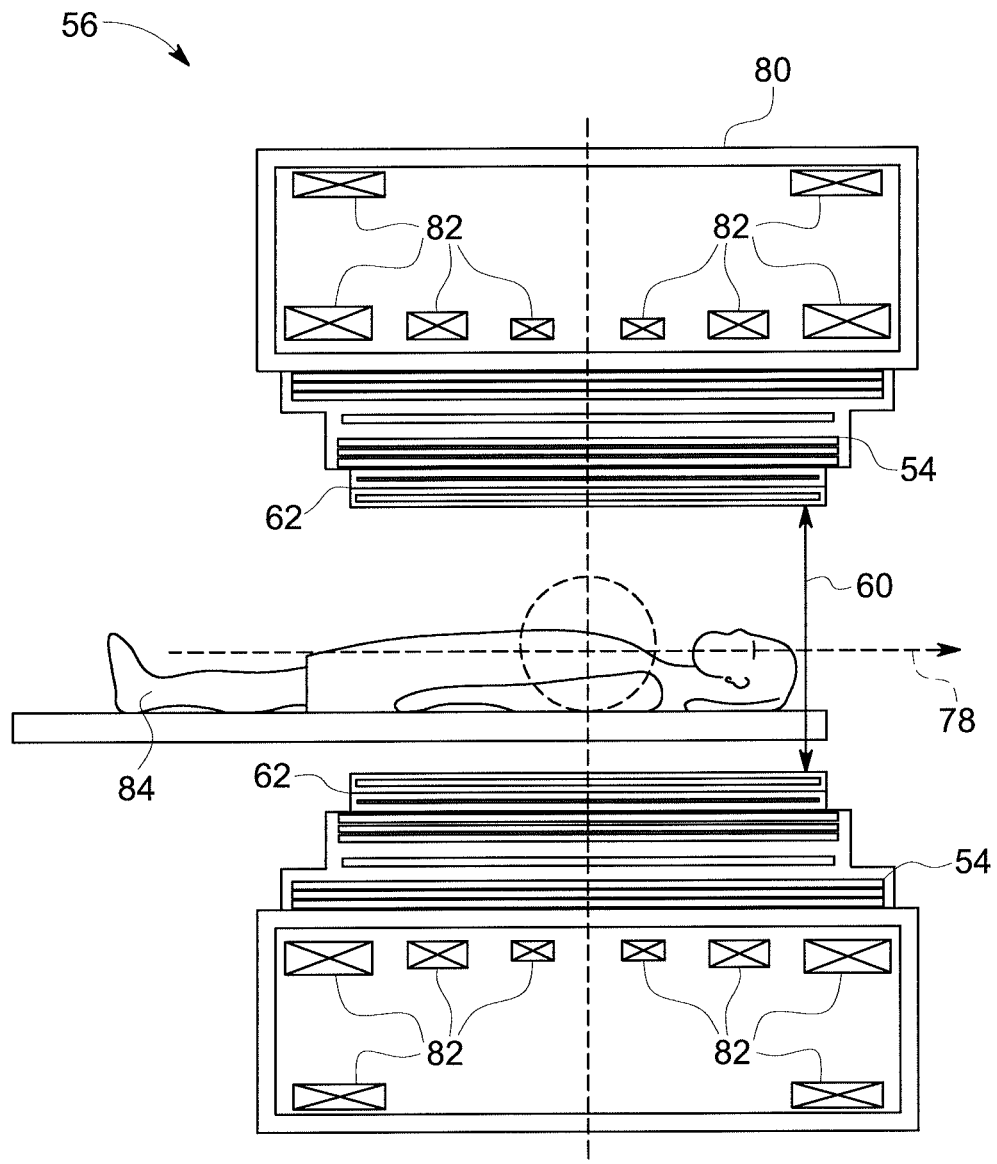
FIG. 2 is a schematic cross-sectional view of a magnet assembly of the MRI system of FIG. 1 in accordance with an embodiment of the invention.

As illustrated in FIG. 2, a schematic side elevation view of the magnet assembly 56 is shown in accordance with an embodiment of the invention. The magnet assembly 56 is cylindrical in shape having a center axis 78. The magnet assembly 56 includes a cryostat 80 and one or more radially aligned longitudinally spaced apart superconductive coils 82 that form the polarizing magnet 58. The superconductive coils 82 are capable of carrying large electrical currents and are designed to create the $B_0$ field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system 10 (FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MM system may also utilize embodiments of the invention described below. As further shown in FIG. 2, a patient/imaged subject 84 is inserted into the magnet assembly 56.

Figure 3:
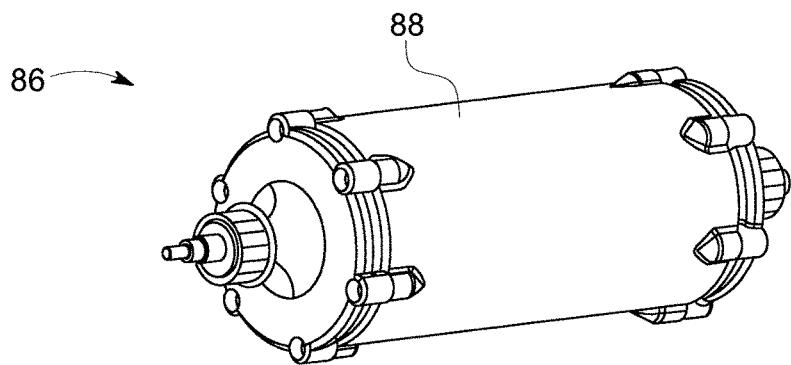
FIG. 3 is a perspective view of a stator-less electric motor for the MRI system of claim 1 in accordance with an embodiment of the invention.
Figure 4:
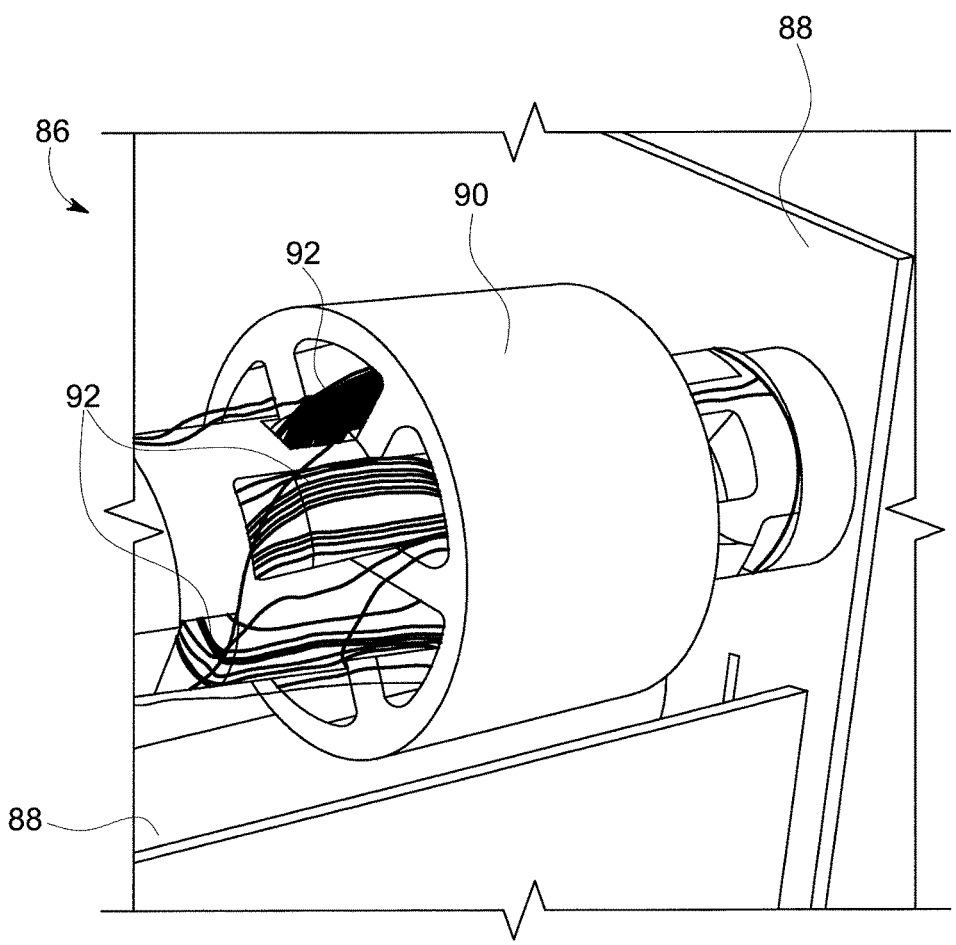
FIG. 4 is a perspective view of a rotor and at least one coil winding of the stator-less electric motor of FIG. 3 in accordance with an embodiment of the invention.

Turning now to FIGS. 3 and 4, the Mill system 10 may include a stator-less electric motor 86 that includes a body 88, a rotor 90 rotatable connected to the body 88, and at least one coil winding 92 disposed on the rotor 90. As will be appreciated, the coil windings 92 may be separate and grouped axial windings.

Figure 5:
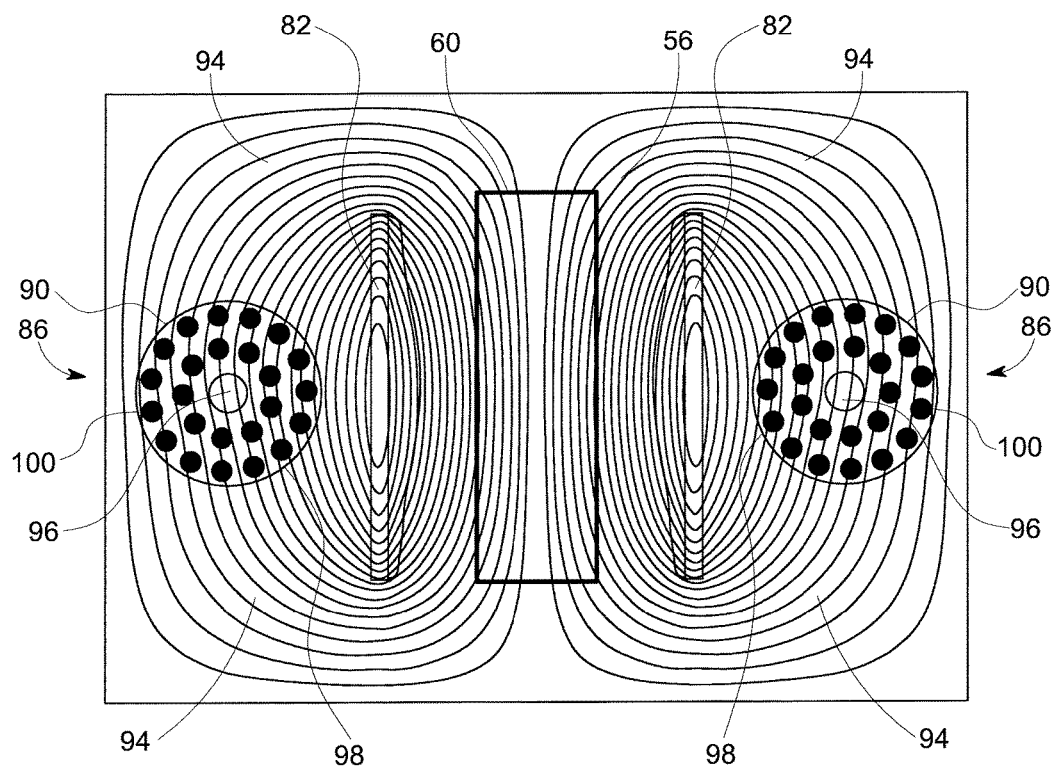
FIG. 5 is a top-down view of the magnet assembly of FIG. 2 depicting a $B_0$ magnetic field generated by superconductive coils of the magnet assembly in accordance with an embodiment of the invention.

Moving to FIG. 5, a top-down view of a horizontal slice through the magnet assembly 56 is shown. As shown in FIG. 5, the stator-less electric motor 86 is disposed in proximity to the magnet assembly 56 such that the $B_0$ field (represented by magnetic field lines 94) created by the superconductive coils 82 passes through the stator-less electric motor 86. As will be appreciated, in embodiments, the part of the $B_0$ field passing through the stator-less electric motor 86 may be a leakage/fringe field on the order of about 0.001 T for a corresponding $B_0$ field on the order of between about 1.5 T to 3 T. As used herein, the terms "leakage field" and "fringe field" refer to the sections of the magnetic field lines 94 of the $B_0$ field which are outside of the bore 60. As further shown in FIGS. 5 and 6, the coil windings 92 are arranged so as to rotate the rotor 90 when energized via an electrical current in the presence of the $B_0$ field. Further, while the magnetic field driving the coil windings 92 is described as being the $B_0$ field, other magnetic fields, which are relatively uniform for extended periods of time, may be utilized.

Figure 6:
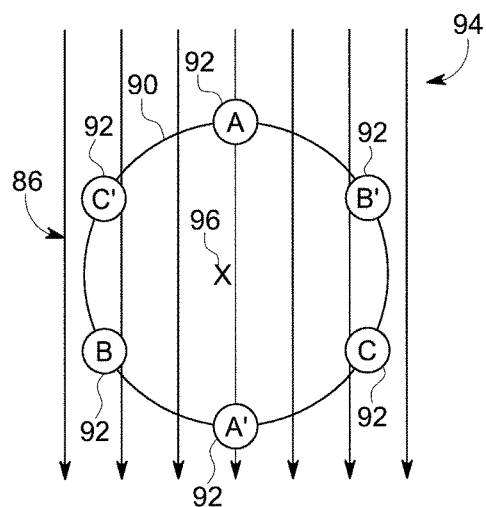
FIG. 6 is a diagram depicting the orientation of a rotor of the stator-less electric motor of FIG. 3 in relation to the $B_0$ magnetic field of FIG. 5 in accordance with an embodiment of the invention.

For example, illustrated in FIG. 6 is in an embodiment of the stator-less electric motor 86 having three sets of coil windings 92 wherein each of the coil windings 92 is depicted as having two matching cross-sectional sections A/A', B/B', and C/C'. As will be appreciated, when the coil windings 92 are energized, electrical current flows in the direction extending out of the drawing sheet at cross-sections A, B, and C, and in the direction extending into the drawing sheet at cross-sections A', B', and C'. In other words, when the coil winding 92 depicted by A and A' is energized, electrical current flows out of the drawing sheet from A, along the portion (not shown) of the coil winding 92 that arcs out of the drawing sheet and connects to A', into the drawing sheet from A', and along the portion (not shown) of the coil winding 92 which arcs into the drawing sheet and connects back to A. Electrical current flows between B to B' and C to C' in a similar manner. As will be understood, when the coil windings 92 are energized in the presences of the $B_0$ field, the coil winding experiences an orthogonal force, i.e., the Lorenz force, based on the relationship between the direction of the current flowing through the coil windings 92 and the direction of the magnetic field lines 94 in accordance with the so called magnetic "Left Hand Rule." Thus, as will be discussed in greater detail below, the energization of the coil windings 92 may be controlled/timed such that the collective orthogonal force experienced by the coil windings 92 causes the rotor 90 to rotate in a clockwise and/or counter-clockwise direction. For example, when the coil windings A/A', B/B', and C/C' are energized as described above in the proper controlled manner, the rotor 90 is caused to rotate in a counter-clockwise direction about an axis 96. As will be appreciated, the direction of rotation of the rotor 90 may be reversed by reversing the direction of the current flowing through coil windings A/A', B/B', and C/C', or by reversing the direction of the magnetic field lines 94.

Figure 7:
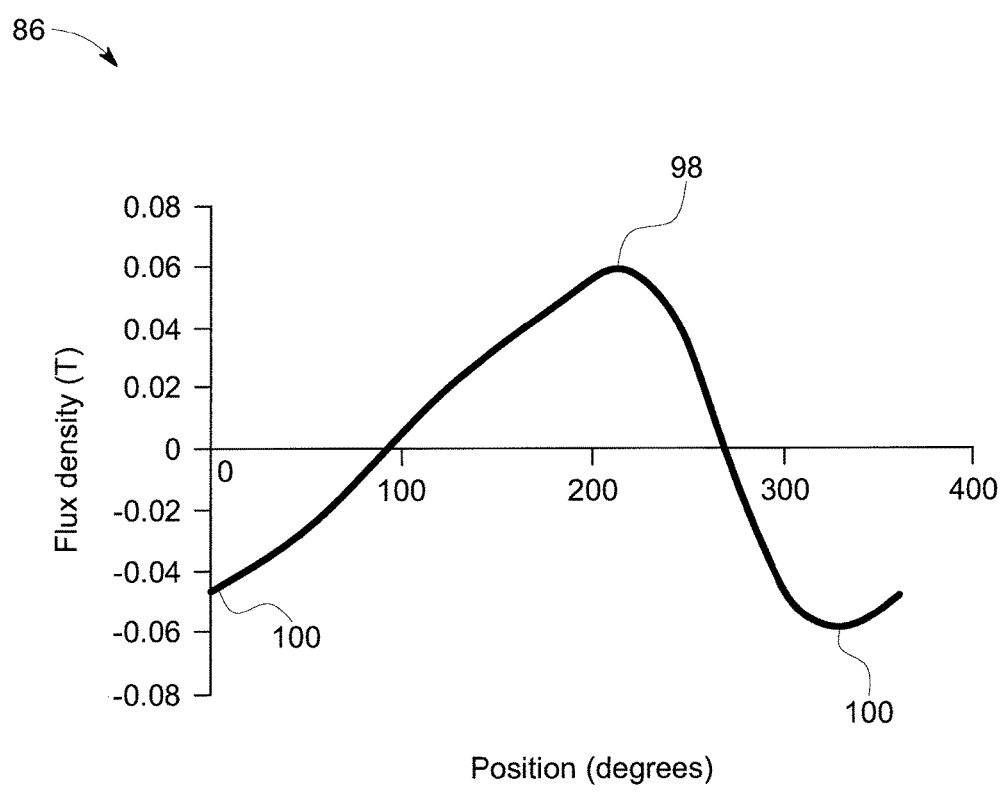
FIG. 7 is a chart that depicts the flux density of the $B_0$ magnetic field of FIG. 5 across the rotor of FIG. 6 in accordance with an embodiment of the invention.

Further, and referring now to FIGS. 5 and 7, as will be appreciated, in embodiments, the control/timing of the coil windings 92 may be based at least in part of the flux density of the $B_0$ field across the rotor 90 (depicted by the chart in FIG. 7) which varies as a result of the distribution of the magnetic field lines 94 (best seen in FIG. 5). For example, as shown in FIG. 7, the flux density across the rotor 90 may be greatest at its closest point 98 to the superconductive coils 82, and lowest at its farthest point 100 from the superconductive coils 82. Thus, the coil windings 92 experiences different levels of force as they rotate on the rotor 90 around the axis 96.

Figure 8:
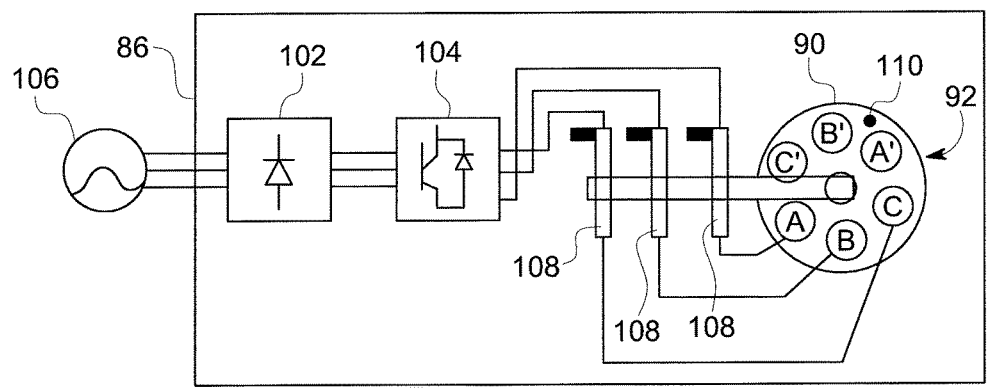
FIG. 8 is a diagram of the stator-less electric motor of FIG. 3, wherein the stator-less electric motor is powered by an alternating current in accordance with an embodiment of the invention.

Moving now to FIG. 8, in embodiments, the coil windings 92 may be energized via an alternating current. In such embodiments, the stator-less electric motor 86 may include a rectifier 102 and an inverter 104 disposed between the rectifier 102 and the coil windings 92. As will be appreciated, the rectifier 102 may provide an electrical current to the inverter 104, and the inverter 104 may control/govern the switching of the electrical current to the coil windings 92. As will be understood, the term "switching," as used herein with respect to an electrical current and the coil windings 92, refers to the timing of energization of the coil windings 92. For example, in embodiments, the alternating current may be a three-phase current, which is indicated in FIG. 8 by the three sets of electrical connections between the rectifier 102, inverter 104, and coil windings 92. The rectifier 102 may receive a source power current from a generator 106, and the inverter 104 may be electrically connected to the coil windings 92 via slip rings 108.

Figure 9:
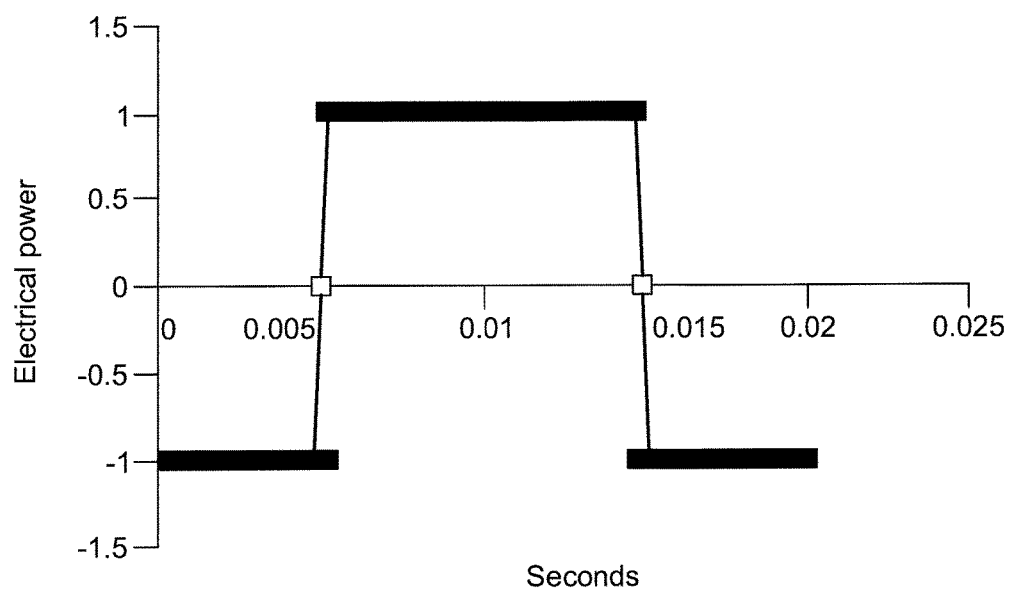
FIG. 9 is a chart that depicts a timing pattern of energizing at least one coil winding of the stator-less electric motor of FIG. 8 in accordance with an embodiment of the invention.

As further shown in FIG. 8, in embodiments, the stator-less electric motor 86 may further include a sensor 110 disposed on the rotor 90 that measures the rotational speed of the rotor 90 about the axis 96. As will be appreciated, the sensor 110 may be any type of rotational speed sensor to include a hall-effect sensor. In such embodiments, the inverter 104 may be in electrical communication with the sensor 110 such that the inverter 104 governs the switching of the electrical current to the coil windings 92 based at least in part on the rotational speed of the rotor 90. For example, the sensor 110 may function as a feedback mechanism that allows the inverter 104 to adjusts/govern the timing of the energization of the coil windings 92 in accordance with the timing pattern depicted in FIG. 9, which as will be appreciated, may correspond to a rotational speed of three-thousand rotations per minute ("RPM").

Figure 10:
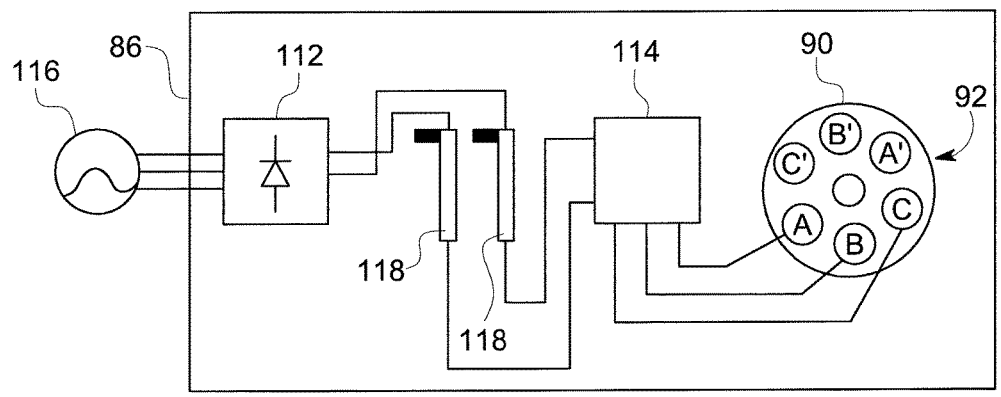
FIG. 10 is a diagram of the stator-less electric motor of FIG. 3, wherein the stator-less electric motor is powered by a direct current and a rotating inverter in accordance with an embodiment of the invention.
Figure 11:
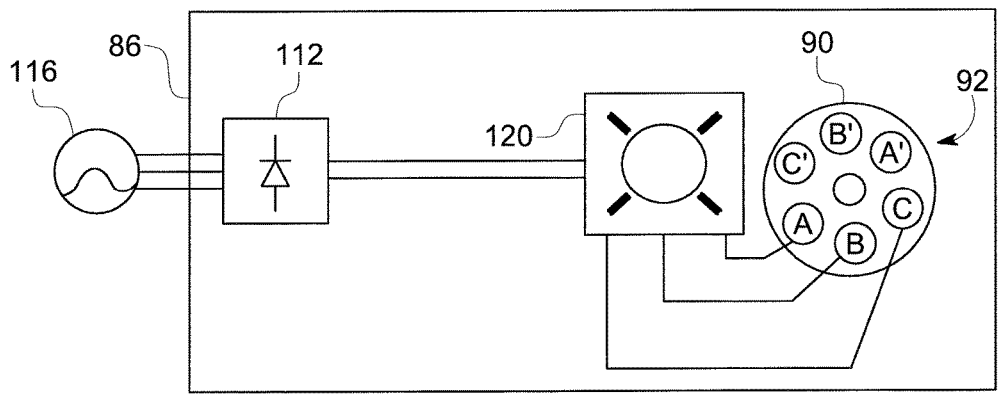
FIG. 11 is a diagram of the stator-less electric motor of FIG. 3, wherein the stator-less electric motor is powered by a direct current and at least one commutator brush in accordance with an embodiment of the invention.

Turning to FIG. 10, in embodiments, the coil windings 92 may be energized via a direct current. In such embodiments, the stator-less electric motor 86 may include a rectifier 112 and a rotating inverter 114 disposed between the rectifier 112 and the coil windings 92. The rectifier 112, which may receive an electrical source current from a generator 116, provides an electrical current to the rotating inverter 114, which in turn governs the switching of the electrical current to the coil windings 92. The rectifier 112 may be electrically connected to the rotating inverter 114 via slip rings 118. Alternatively, and as shown in FIG. 11, in embodiments wherein the coil windings 92 are energized via a direct current, the stator-less electric motor 86 may include at least one commutator brush 120, e.g., a clocked commutator, in place of the rotating inverter 114, which govern the switching of the electrical current to the coil windings 92.

Figure 12:
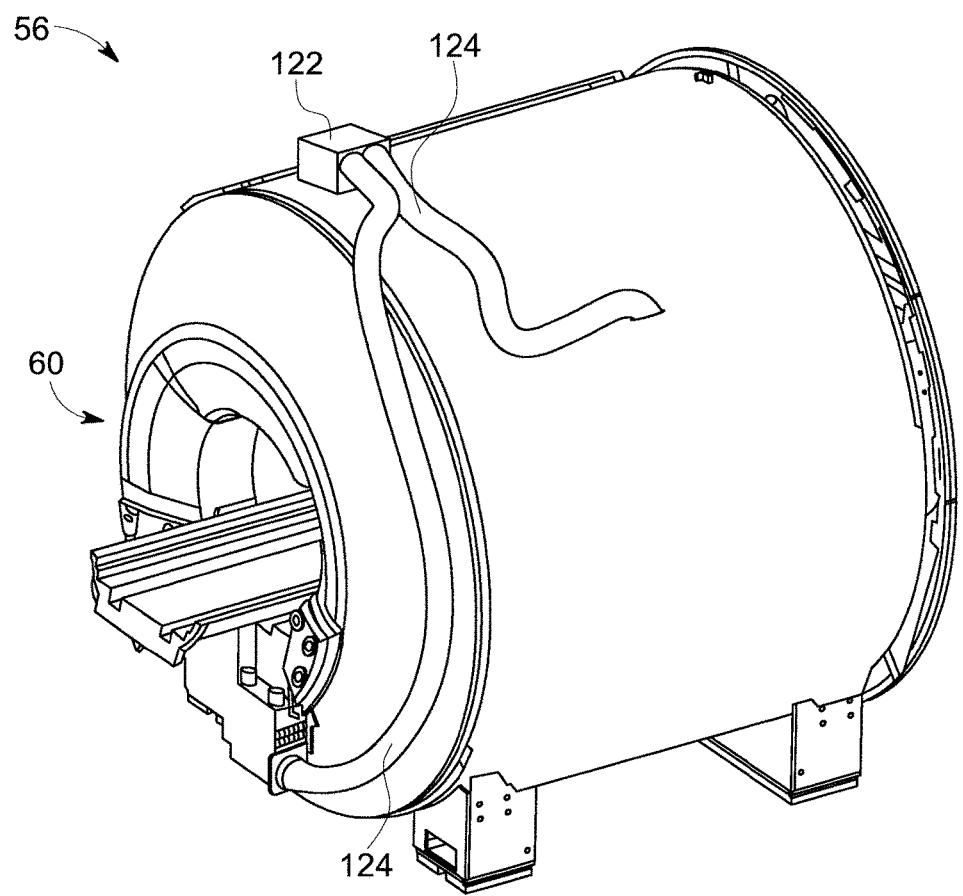
FIG. 12 is a perspective view of the magnet assembly of FIG. 2 in accordance with an embodiment of the invention.

As shown in FIG. 12, in embodiments, the stator-less electric motor 86 may drive a blower/liquid pump 122 that cools a patient within the bore 60, and/or one or more electrical components of the MRI system 10. For example, the blower/liquid pump 122 may be operative to move air, coolant, and/or hydraulic fluid through a series of ducts/pipes 124 that distribute the air, coolant and/or hydraulic fluid to various parts of the magnet assembly 56.

Further, as will be appreciated, in embodiments, the stator-less electric motor 86 may be made from materials that do not experience an induced magnetic force in the presence of the $B_0$ field when the coil windings 92 are not energized. For example, the stator-less electric motor 86 may be made from materials such as plastics and/or copper that are not diamagnetic, paramagnetic, or ferromagnetic.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory ("RAM") and read-only memory ("ROM"). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a stator-less electric motor for an MRI system is provided. The stator-less electric motor includes a body, a rotor rotatable connected to the body, and at least one coil winding disposed on the rotor. The at least one coil winding is arranged so as to rotate the rotor when energized via an electrical current in the presence of a magnetic field generated by a magnet assembly of the MRI system. In certain embodiments, the magnetic field is a leakage field outside of a bore of the magnet assembly. In certain embodiments, the electrical current is an alternating current. In certain embodiments, the stator-less electric motor further includes a sensor disposed on the rotor and operative to measure a rotational speed of the rotor, a rectifier operative to provide the electrical current, and an inverter disposed between the rectifier and the at least one coil winding. The inverter is operative to govern the switching of the electrical current to the at least one coil winding based at least in part on the rotational speed of the rotor. In certain embodiments, the electrical current is a direct current. In certain embodiments, the stator-less electric motor further includes a rectifier operative to provide the electrical current, and a rotating inverter disposed between the rectifier and the at least one coil winding. The rotating inverter is operative to govern the switching of the electrical current to the at least one coil winding. In certain embodiments, the stator-less electric motor further includes at least one commutator brush operative to govern the switching of the electrical current to the at least one coil winding. In certain embodiments, the rotor is operative to drive at least one of a blower and a liquid pump. In certain embodiments, the blower is operative to cool at least one of: a patient disposed within a bore of the magnet assembly; and one or more electrical components of the MRI system. In certain embodiments, the magnetic field does not induce a magnetic force in the stator-less motor when the at least one coil winding is not energized.

Other embodiments provide for a method of powering a stator-less electric motor. The method includes: generating a magnetic field via a magnet assembly of an MRI system; energizing at least one coil winding via an electrical current, the at least one coil winding disposed within the magnetic field on a rotor rotatable connected to a body of the stator-less electric motor; and rotating the rotor via the one or more energized coil windings in the presence of the magnetic field. In certain embodiments, the magnetic field is a leakage field outside of a bore of the magnet assembly. In certain embodiments, the electrical current is an alternating current, and the method further includes: measuring a rotational speed of the rotor via a sensor disposed on the rotor; providing the electrical current to an inverter via a rectifier, the inverter disposed between the rectifier and the at least one coil winding; and switching the electrical current to the at least one coil winding via the inverter based at least in part on the rotational speed of the rotor. In certain embodiments, the electrical current is a direct current and the method further includes: providing the electrical current to a rotating inverter via a rectifier, the rotating inverter disposed between the rectifier and the at least one coil winding; and switching the electrical current to the at least one coil winding via the rotating inverter. In certain embodiments, the electrical current is a direct current and the method further includes: switching the electrical current to the at least one coil winding via at least one commutator brush. In certain embodiments, the method further includes driving at least one of a blower and a liquid pump via the rotor. In certain embodiments, the blower cools at least one of: a patient within a bore of the magnet assembly; and one or more electrical components of the Mill system. In certain embodiments, the magnetic field does not induce a magnetic force in the stator-less motor when the at least one coil winding is not energized.

Yet still other embodiments provide for an MRI system. The MRI system includes a magnet assembly operative to generate a magnetic field, and a stator-less electric motor. The stator-less motor includes a body, a rotor ratably connected to the body, and at least one coil winding disposed on the rotor. The at least one coil winding is arranged so as to rotate the rotor when energized via an electrical current in the presence of the magnetic field. In certain embodiments, the magnetic field does not induce a magnetic force in the stator-less motor when the at least one coil winding is not energized.

Accordingly, as will be appreciated, by utilizing the $B_0$ field generated by the superconductive coils 82 of an MRI system 10, some embodiments of the invention provide for a stator-less electric motor 86 that does not experience a magnetic force when the coil windings 92 are not energized. Thus, some embodiments of the present invention provide for electric motors that can be utilized in close proximity to strong magnets, e.g., MRI superconductive coils, with a reduced risk that such electric motors will be violently accelerated towards the strong magnets. Thus, some embodiments of the invention provide for safer electric motors for use in MRI systems. Additionally, some embodiments provide for an electric motor that can be disposed at numerous locations within an MRI system, thus allowing airflow, via blowers, to be created locally as needed, which in turn reduces the need for lengthy hoses and/or complex airflow routing.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A stator-less electric motor for an MRI system comprising:
    a body;
    a rotor rotatably connected to the body;
    at least one coil winding disposed on the rotor; and
    wherein
        the at least one coil winding is arranged so as to rotate the rotor when energized via an electrical current in the presence of a magnetic field generated by a magnet assembly of the MRI system; and
        the magnetic field is a leakage field outside of a bore of the magnet assembly.

2. The stator-less electric motor of claim 1, wherein the electrical current is an alternating current.

3. The stator-less electric motor of claim 2 further comprising:
    a sensor disposed on the rotor and operative to measure a rotational speed of the rotor;
    a rectifier operative to provide the electrical current;
    an inverter disposed between the rectifier and the at least one coil winding and operative to govern the switching of the electrical current to the at least one coil winding based at least in part on the rotational speed of the rotor.

4. The stator-less electric motor of claim 1, wherein the electrical current is a direct current.

5. The stator-less electric motor of claim 4 further comprising:
    a rectifier operative to provide the electrical current; and
    a rotating inverter disposed between the rectifier and the at least one coil winding and operative to govern the switching of the electrical current to the at least one coil winding.

6. The stator-less electric motor of claim 4 further comprising:
    at least one commutator brush operative to govern the switching of the electrical current to the at least one coil winding.

7. The stator-less electric motor of claim 1, wherein the rotor is operative to drive at least one of a blower and a liquid pump.

8. The stator-less electric motor of claim 7, wherein the blower is operative to cool at least one of:
    a patient disposed within the bore of the magnet assembly; and
    one or more electrical components of the MRI system.

9. The stator-less electric motor of claim 1, wherein the magnetic field does not induce a magnetic force in the stator-less motor when the at least one coil winding is not energized.

10. A method of powering a stator-less electric motor comprising:
    generating a magnetic field via a magnet assembly of an MRI system;
    energizing at least one coil winding via an electrical current, the at least one coil winding disposed within the magnetic field on a rotor rotatably connected to a body of the stator-less electric motor;
    rotating the rotor via the at least one energized coil winding in the presence of the magnetic field; and wherein the magnetic field is a leakage field outside of a bore of the magnet assembly.

11. The method of claim 10, wherein the electrical current is an alternating current, and the method further comprises:
measuring a rotational speed of the rotor via a sensor disposed on the rotor;
providing the electrical current to an inverter via a rectifier, the inverter disposed between the rectifier and the at least one coil winding; and
switching the electrical current to the at least one coil winding via the inverter based at least in part on the rotational speed of the rotor.

12. The method of claim 10, wherein the electrical current is a direct current and the method further comprises:
providing the electrical current to a rotating inverter via a rectifier, the rotating inverter disposed between the rectifier and the at least one coil winding; and
switching the electrical current to the at least one coil winding via the rotating inverter.

13. The method of claim 10, wherein the electrical current is a direct current and the method further comprises:
switching the electrical current to the at least one coil winding via at least one commutator brush.

14. The method of claim 10 further comprising:
driving at least one of a blower and a liquid pump via the rotor.

15. The method of claim 14 wherein the blower cools at least one of:
a patient within the bore of the magnet assembly; and
one or more electrical components of the MRI system.

16. The method of claim 10, wherein the magnetic field does not induce a magnetic force in the stator-less motor when the at least one coil winding is not energized.

17. An MRI system comprising:
a magnet assembly operative to generate a magnetic field;
a stator-less electric motor that includes:
a body;
a rotor rotatably connected to the body; and
at least one coil winding disposed on the rotor; and
wherein
the at least one coil winding is arranged so as to rotate the rotor when energized via an electrical current in the presence of the magnetic field, and
the magnetic field is a leakage field outside of a bore of the magnet assembly.

18. The MRI system of claim 17, wherein the magnetic field does not induce a magnetic force in the stator-less motor when the at least one coil winding is not energized.

19. A stator-less electric motor for an MRI system comprising:
a body;
a rotor rotatably connected to the body and operative to drive at least one of a blower and a liquid pump;
at least one coil winding disposed on the rotor; and
wherein the at least one coil winding is arranged so as to rotate the rotor when energized via an electrical current in the presence of a magnetic field generated by a magnet assembly of the MRI system.

20. A stator-less electric motor for an MRI system comprising:
a body;
a rotor rotatably connected to the body;
at least one coil winding disposed on the rotor;
a sensor disposed on the rotor and operative to measure a rotational speed of the rotor;
a rectifier operative to provide an alternating electrical current;
an inverter disposed between the rectifier and the at least one coil winding; and
wherein
the at least one coil winding is arranged so as to rotate the rotor when energized via the alternating electrical current in the presence of a magnetic field generated by a magnet assembly of the MRI system, and
the inverter is operative to govern the switching of the electrical current to the at least one coil winding based at least in part on the rotational speed of the rotor.

21. A method of powering a stator-less electric motor comprising:
generating a magnetic field via a magnet assembly of an MRI system;
energizing at least one coil winding via an electrical current, the at least one coil winding disposed within the magnetic field on a rotor rotatably connected to a body of the stator-less electric motor;
rotating the rotor via the at least one energized coil windings in the presence of the magnetic field; and
driving at least one of a blower and a liquid pump via the rotor.

22. A method of powering a stator-less electric motor comprising:
generating a magnetic field via a magnet assembly of an MRI system;
providing a direct electrical current to a rotating inverter via a rectifier, the rotating inverter disposed between the rectifier and at least one coil winding disposed within the magnetic field on a rotor rotatably connected to a body of the stator-less electric motor;
energizing the at least one coil winding via the direct electrical current;
rotating the rotor via the at least one energized coil winding in the presence of the magnetic field; and
switching the electrical current to the at least one coil winding via the rotating inverter.

* * * * *